United States Patent
Woodby et al.

(10) Patent No.: US 11,464,179 B2
(45) Date of Patent: Oct. 11, 2022

(54) SYSTEMS PROVIDING IRRIGATION OPTIMIZATION USING SENSOR NETWORKS AND SOIL MOISTURE MODELING

(71) Applicant: FarmX Inc., Mountain View, CA (US)

(72) Inventors: Robin Lucien Woodby, Berkeley, CA (US); Kentaro Fitzgerald Kuwata, Redwood City, CA (US); William Eugene Jennings, San Jose, CA (US)

(73) Assignee: FarmX Inc., Mountain View, CA (US)

( * ) Notice: Subject to any disclaimer, the term of this patent is extended or adjusted under 35 U.S.C. 154(b) by 0 days.

(21) Appl. No.: 16/945,797

(22) Filed: Jul. 31, 2020

(65) Prior Publication Data
US 2022/0030786 A1 Feb. 3, 2022

(51) Int. Cl.
*A01G 25/16* (2006.01)
*G01N 33/24* (2006.01)
*G05B 19/042* (2006.01)
*G01W 1/02* (2006.01)

(52) U.S. Cl.
CPC ......... *A01G 25/167* (2013.01); *G01N 33/246* (2013.01); *G01W 1/02* (2013.01); *G05B 19/042* (2013.01); *G01N 2033/245* (2013.01); *G05B 2219/2625* (2013.01)

(58) Field of Classification Search
CPC ............... A01G 25/167; G01N 33/246; G01N 2033/245; G05B 19/042; G05B 2219/2625; G01W 1/02
See application file for complete search history.

(56) References Cited

U.S. PATENT DOCUMENTS

| | | |
|---|---|---|
| RE31,023 E | 9/1982 | Hall, III |
| 4,590,477 A | 5/1986 | Regnier et al. |
| 4,654,598 A | 3/1987 | Arulanandan et al. |

(Continued)

FOREIGN PATENT DOCUMENTS

| | | | |
|---|---|---|---|
| CN | 103308665 A | * | 9/2013 |
| JP | H08115300 A | | 5/1996 |

(Continued)

OTHER PUBLICATIONS

EnviroSCAN Probe, [retrieved on Dec. 14, 2016], Retrieved from the Internet: <Url:http://www.sentek.com.au/products/enviro-scan-probe.asp>, 3 pages.

(Continued)

*Primary Examiner* — Chad G Erdman
(74) *Attorney, Agent, or Firm* — Carr & Ferrell LLP

(57) ABSTRACT

Systems and methods for providing irrigation water to a soil depth of a crop rootzone in a plurality of crop fields using a sensor network and soil moisture modeling are provided. In various embodiments methods include receiving data from a sensor network in a first crop field and determining a soil moisture model using data from the sensor network in the first field. Various embodiments further include determining a first field irrigation time using the soil moisture model, the first field irrigation time providing irrigation water to a soil depth of the crop rootzone above a Wilting Point (WP) and below a Field Capacity (FC) of soil in the first field, and applying the soil moisture model to a second field.

17 Claims, 5 Drawing Sheets

(56) References Cited

U.S. PATENT DOCUMENTS

| | | | |
|---|---|---|---|
| 5,418,466 A | 5/1995 | Watson et al. | |
| 5,445,178 A | 8/1995 | Feuer | |
| 5,696,671 A * | 12/1997 | Oliver | A01G 25/16 |
| | | | 700/284 |
| 6,014,029 A | 1/2000 | Soto et al. | |
| 6,720,908 B1 | 4/2004 | Puglia | |
| 6,891,444 B2 | 5/2005 | Jacobsson et al. | |
| 6,977,351 B1 | 12/2005 | Woytowitz | |
| 7,836,910 B2 | 11/2010 | Dresselhaus et al. | |
| 8,682,494 B1 | 3/2014 | Magro et al. | |
| 9,107,354 B2 * | 8/2015 | Martin | A01G 25/167 |
| 10,509,378 B2 | 12/2019 | Jennings et al. | |
| 10,533,956 B2 | 1/2020 | Jennings | |
| 10,746,720 B2 | 8/2020 | Jennings | |
| 10,983,489 B2 | 4/2021 | Jennings et al. | |
| 11,166,404 B2 | 11/2021 | Oaklander et al. | |
| 2002/0170229 A1 | 11/2002 | Ton et al. | |
| 2004/0145379 A1 | 7/2004 | Buss | |
| 2004/0239338 A1 | 12/2004 | Jonsson et al. | |
| 2006/0057997 A1 | 3/2006 | Hausdorf et al. | |
| 2006/0144437 A1 | 7/2006 | Dresselhaus et al. | |
| 2006/0227661 A1 | 10/2006 | Shook et al. | |
| 2009/0326723 A1 | 12/2009 | Moore et al. | |
| 2010/0257633 A1 | 10/2010 | Pogson et al. | |
| 2012/0084115 A1 | 4/2012 | Cline et al. | |
| 2012/0306257 A1 | 12/2012 | Silversides et al. | |
| 2013/0341420 A1 | 12/2013 | Lister et al. | |
| 2014/0183573 A1 | 1/2014 | Avey | |
| 2014/0088770 A1 | 3/2014 | Masters et al. | |
| 2014/0117468 A1 | 5/2014 | Parris et al. | |
| 2014/0326801 A1 | 11/2014 | Upadhyaya et al. | |
| 2015/0081058 A1 | 3/2015 | Oliver et al. | |
| 2015/0247787 A1 | 9/2015 | Yeomans | |
| 2015/0268218 A1 | 9/2015 | Troxler | |
| 2015/0278719 A1 | 10/2015 | Schueller et al. | |
| 2015/0301536 A1 | 10/2015 | Martinez | |
| 2016/0037709 A1 | 2/2016 | Sauder et al. | |
| 2016/0135389 A1 | 5/2016 | Ersavas et al. | |
| 2016/0183484 A1 | 6/2016 | Richings, Sr. et al. | |
| 2016/0202227 A1 | 7/2016 | Mathur et al. | |
| 2016/0306759 A1 | 10/2016 | Ham | |
| 2016/0327511 A1 | 11/2016 | Wenzel et al. | |
| 2017/0108452 A1 | 4/2017 | Carlson | |
| 2017/0172077 A1 | 6/2017 | Wouhaybi et al. | |
| 2017/0176572 A1 | 6/2017 | Charvat et al. | |
| 2017/0311559 A1 | 11/2017 | Ebert et al. | |
| 2018/0080861 A1 | 3/2018 | Lafian | |
| 2018/0129175 A1 | 5/2018 | Jennings et al. | |
| 2018/0146631 A1 | 5/2018 | Haran et al. | |
| 2018/0146632 A1 | 5/2018 | Meron | |
| 2018/0164230 A1 | 6/2018 | Jennings | |
| 2018/0164762 A1 | 6/2018 | Mewes et al. | |
| 2018/0202988 A1 | 7/2018 | Jennings | |
| 2018/0252694 A1 | 9/2018 | Mase et al. | |
| 2018/0259496 A1 | 9/2018 | McPeek | |
| 2018/0368339 A1 * | 12/2018 | van der Lee | G01N 33/246 |
| 2020/0026250 A1 | 1/2020 | Jennings et al. | |
| 2020/0068784 A1 | 3/2020 | Oaklander et al. | |
| 2020/0296906 A1 * | 9/2020 | Sun | A01G 25/165 |
| 2020/0383284 A1 * | 12/2020 | Larsen | G01W 1/10 |
| 2021/0073925 A1 * | 3/2021 | Singh | G06Q 50/02 |
| 2021/0208124 A1 | 7/2021 | Jennings | |
| 2021/0232108 A1 | 7/2021 | Jennings et al. | |
| 2022/0124964 A1 | 4/2022 | Oaklander et al. | |

FOREIGN PATENT DOCUMENTS

| | | |
|---|---|---|
| JP | 2005198560 A | 7/2005 |
| WO | WO2016110832 A1 | 7/2016 |
| WO | WO2018085452 A1 | 5/2018 |

OTHER PUBLICATIONS

Liquid Sensing at Radio Frequencies, Complex impedance measurement of liquid samples as a function of frequency, [retrieved on Jan. 13, 2017] Microwave Journal, Thomas J. Warnagiris, Sep. 1, 2000, (http://www.microwavejournal.com/articles/3038-liquid-sensing-at-radio-frequencies), 9 pages.

"International Search Report" and "Written Opinion of the International Searching Authority", Patent Cooperation Treaty Application No. PCT/US2017/059597, dated Jan. 25, 2018, 9 pages.

Berni et al., "Mapping Canopy Conductance and CWSI in Olive Orchards Using High Resolution Thermal Remote Sensing Imagery", in: Remote Sensing Environment 113 [online], Jun. 28, 2009 [retrieved on Jan. 4, 2018], Retrieved from the Internet: <URL:https://www.sciencedirect.com/science/article/pii/S0034425709002090>, pp. 2380-2388.

Smith, Adam Brook, "Soil Moisture Monitoring with Ground-Based Gravity Data," Dissertation University of Melbourne, Department of Infrastructure Engineers, 2013, 397 pages.

* cited by examiner

SYSTEMS PROVIDING IRRIGATION OPTIMIZATION USING SENSOR NETWORKS AND SOIL MOISTURE MODELING

FIELD OF THE TECHNOLOGY

Embodiments of the disclosure relate to irrigation optimization. In particular, the present disclosure relates to systems and methods providing irrigation optimization using sensor networks and soil moisture modeling.

BACKGROUND

The approaches described in this section could be pursued, but are not necessarily approaches that have previously been conceived or pursued. Therefore, unless otherwise indicated, it should not be assumed that any of the approaches described in this section qualify as prior art merely by virtue of their inclusion in this section.

Irrigation is a method of withdrawing water from a water source and providing the water to a crop field. Irrigation is used for various instances including increasing crop yields, maintaining a landscape, greening, and the like. About eighty percent of irrigation water used in the United States is used for agricultural irrigation, and more than seventy percent of the irrigation water may be irrigation accumulated in the western region of the United States. For agricultural production, irrigation is not only used for increasing yields but also for applications such as protecting crop from frost damage, suppressing weeds, and preventing soil compaction. Irrigation is effective and indispensable for establishing stable crop production. However, water is becoming scarcer because of the frequent occurrence of drought associated with climate change as well as sinking of groundwater sources due to land subsidence, among other factors. Thus, irrigation costs are increasing year-by-year because of the scarcity of water. Furthermore, the scarcity of water is threatening sustainable development of agriculture. Therefore, there is a need to use the limited water resources more efficiently from the viewpoint of the natural environment as well as for economic management by farmers. Consequently, there is a need to reduce irrigation costs associated with agricultural irrigation without losing productivity to provide improved profits for agriculture business and to achieve sustainable agriculture by using irrigation water more efficiently to save water for environmental reasons.

SUMMARY

According to some embodiments, the present technology is directed to systems and methods for providing irrigation water to a soil depth of a crop rootzone in a plurality of crop fields using a sensor network and soil moisture modeling. In some embodiments the system comprises: (A) a sensor network in a first crop field. In some instances, the sensor network, comprises: (i) a soil moisture sensor in the first crop field; (ii) a water added sensor in the first crop field; and (iii) a meteorological elements sensor in the first crop field. The system further comprises: (B) at least one processor; and (C) a memory storing processor-executable instructions, wherein the at least one processor is configured to implement the following operations upon executing the processor-executable instructions: (a) determining a soil moisture model using data from the sensor network in the first field; (b) determining a first field irrigation time using the soil moisture model, the first field irrigation time providing irrigation water to a soil depth of the crop rootzone above a Wilting Point (WP) and below a Field Capacity (FC) of soil in the first field; (c) applying the soil moisture model to a second field; and (d) determining a second field irrigation time using the soil moisture model, the second field irrigation time providing irrigation water to a soil depth of the crop rootzone above a Wilting Point (WP) and below a Field Capacity (FC) of soil in the second field; and (D) an irrigation system providing irrigation water in the first field for the first field irrigation time to a soil depth of the crop rootzone above a Wilting Point (WP) and below a Field Capacity (FC) of soil in the first field, and providing irrigation water in the second field for the second field irrigation time to a soil depth of the crop rootzone above a Wilting Point (WP) and below a Field Capacity (FC) of soil in the second field.

In some embodiments the water added sensor measures an actual amount of water added to a field. In various embodiments the meteorological elements sensor measures at least one of temperature, precipitation, solar radiation, relative humidity, and wind speed.

In some embodiments the soil moisture sensor measures an amount of moisture contained in the soil at a plurality of different depths in the soil at the first field. In some instances, the plurality of different depths in the soil at the first field include a soil depth above the crop rootzone, a soil depth at the crop rootzone, and a soil depth below the crop rootzone.

In some embodiments the first field irrigation time and the second field irrigation time provide irrigation water above field capacity for the soil depth at the crop rootzone resulting in irrigation water percolation to the crop rootzone.

In some embodiments the first field irrigation time and the second field irrigation time provide irrigation water below field capacity for the soil depth at the crop rootzone preventing irrigation water percolation to the soil depth below the crop rootzone thereby saving irrigation water.

According to exemplary embodiments the determining the soil moisture model comprises: determining current soil moisture, infiltration, percolation, and evapotranspiration at the soil depth above the crop rootzone in the first field using the data from the sensor network in the first field; and determining soil moisture at the soil depth above the crop rootzone in the second field using the current soil moisture, the infiltration, the percolation, and the evapotranspiration at the soil depth above the crop rootzone in the first field.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

DETAILED DESCRIPTION

Figure 1:
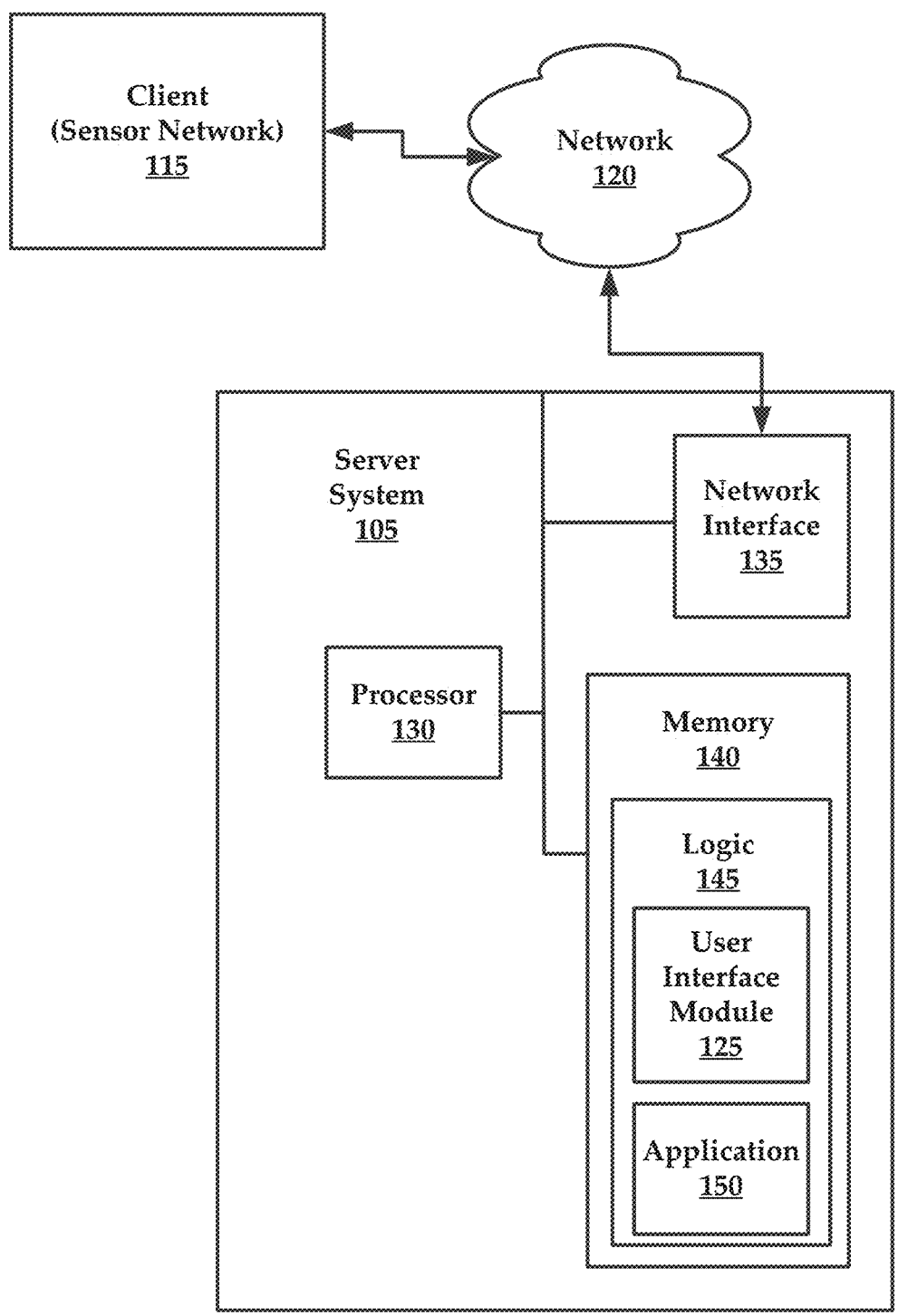
FIG. 1 is a schematic diagram of an exemplary computing architecture that can be used to practice aspects of the present technology.

In the following description, for purposes of explanation, numerous specific details are set forth in order to provide a thorough understanding of the disclosure. It will be apparent, however, to one skilled in the art, that the disclosure may be practiced without these specific details. In other instances, structures and devices may be shown in block diagram form only in order to avoid obscuring the disclosure. It should be understood that the disclosed embodiments are merely exemplary of the invention, which may be embodied in multiple forms. Those details disclosed herein are not to be interpreted in any form as limiting, but as the basis for the claims.

Various exemplary embodiments described and illustrated herein relate to using irrigation water efficiently by using a sensor network, soil moisture modeling and interpolation by remote sensing. The present technology provides systems and methods for maintaining irrigation water to a depth of a crop rootzone in a plurality of fields using a sensor network, soil moisture modeling, and interpolation by remote sensing. In order to use irrigation water effectively, it may be necessary to spray an appropriate amount of water at a suitable time according to the conditions of crops and soil. For that purpose, it is necessary to know the current condition of the crops and the soil. In various embodiments the sensor network is a sensor infrastructure that measures the current conditions of the crops and the soil in near real-time with sensors installed in a field. By utilizing data collected by sensor networks, a model amount of water movement in the soil may be constructed using soil moisture modeling. Soil moisture modeling models movement of water in the soil and may be used to calculate how long irrigation water will take to reach a depth of a crop rootzone and to estimate an appropriate irrigation time for a crop. A crop rootzone is a depth in the soil when roots of the crop are present and irrigation water to the crop is used most efficiently when the water reaches the depth of a crop rootzone. In contrast, deep percolation, where water moves below the depth of the crop root zone in the soil, can occur when an irrigation system operates for too long or if the water delivery rate is too high, resulting is the irrigation water being wasted and not being used efficiently.

In various embodiments, a sensor network may require hardware installation in a field. To control costs on hardware expenditures, there is an upper limit on the number of hardware installations for farmers. Therefore, a problem exists because it is difficult to apply the soil moisture modeling to the entire area of a field because there will be locations in the field where sensors are not installed. To solve this problem, information necessary for the soil moisture modeling is acquired at the non-sensor locations by interpolation by remote sensing. In other words, interpolation technology using remote sensing.

Using exemplary embodiments of the present technology, a sensor network comprising twenty sensors was constructed into a sensor network in a pistachio ranch in the Central Valley of California. The sensor network collected a plurality of data feeds including soil moisture data, water pressure data, weather data, and dendrometer data every few minutes to monitor all irrigation events, and a crop (i.e., pistachio trees) environment in a field on the pistachio ranch. By using this data to not make water pass a soil depth of a crop rootzone (i.e., a soil depth of a pistachio tree rootzone), the farmers achieved a seven percent reduction of irrigation costs. In other words, embodiments of the present technology avoided deep percolation by irrigation water, where water moves below the depth of the crop root zone (i.e., the soil depth of a pistachio tree rootzone), which occurs when the irrigation system operates for too long or if the water delivery rate is too high. In exemplary embodiments, scheduling of irrigation based on the plurality of data feeds may be established manually. In some embodiments soil moisture modeling and interpolation by remote sensing allows farmers to automate decision making of appropriate irrigation planning. By combining a sensor network, soil moisture modeling, and interpolation by remote sensing, irrigation across the crop field (i.e., field of pistachio trees) was optimized and irrigation costs are reduced.

In various embodiments a sensor network comprises a plurality of sensors to measure a plurality of environmental elements. In some instances, the plurality of environmental elements include soil moisture, infiltration, percolation, and evapotranspiration.

In some embodiments the sensor network includes a soil moisture sensor. The soil moisture sensor may measure the amount of water or moisture contained in the soil. The soil moisture sensor may have multiple observation points at different depths in the soil. Soil moisture data from the soil moisture sensor is important information to calculate the minimum water content required for preventing crop growth inhibition by water stress from the current soil water content.

In some embodiments the sensor network includes a water added sensor. The water added sensor measures an actual amount of water putted or added to a field. A water added sensor is used to verify that an amount of water sprayed onto a field matches the amount of water needed by the crop in that field.

In some embodiments the sensor network includes a meteorological elements sensor. The meteorological elements sensor may measure temperature, precipitation, solar radiation, relative humidity, wind speed, and the like. By using meteorological elements data, evapotranspiration (ET) which corresponds to an amount of water required for photosynthesis activity of a crop, may be calculated based on several methods such as using the FAO Penman-Monteith equation.

In some embodiments the sensor network may continuously measure the environmental elements including the soil moisture, the amount of water added to a field, and the meteorological elements. In various embodiments the sensor network may measure the environmental elements at a specific time-interval such as one-minute, five-minutes, thirty-minutes, and so forth, and aggregate the specific time interval into a time-period. For example, the time-period may be one hour.

FIG. 1 illustrates an exemplary architecture for practicing aspects of the present technology. The architecture comprises a server system, hereinafter "system 105" that is configured to provide various functionalities, which are described in greater detail throughout the present disclosure. Generally, the system 105 is configured to communicate with a client (sensor network), such as client (sensor network) 115. The client (sensor network) 115 may include, for example, a sensor system or other similar computing devices. In various embodiments a sensor network comprises a plurality of sensors to measure a plurality of environmental elements. In some instances, the plurality of environmental elements include soil moisture, infiltration, percolation, and evapotranspiration. An example of a computing device that can be utilized in accordance with the present technology is described in greater detail with respect to FIG. 5.

The system 105 may communicatively couple with the client (sensor network) 115 via a public or private network, such as network 120. Suitable networks may include or interface with any one or more of, for instance, a local intranet, a PAN (Personal Area Network), a LAN (Local Area Network), a WAN (Wide Area Network), a MAN (Metropolitan Area Network), a virtual private network (VPN), a storage area network (SAN), a frame relay connection, an Advanced Intelligent Network (AIN) connection, a synchronous optical network (SONET) connection, a digital T1, T3, E1 or E3 line, Digital Data Service (DDS) connection, DSL (Digital Subscriber Line) connection, an Ethernet connection, an ISDN (Integrated Services Digital Network) line, a dial-up port such as a V.90, V.34 or V.34bis analog modem connection, a cable modem, an ATM (Asynchronous Transfer Mode) connection, or an FDDI (Fiber Distributed Data Interface) or CDDI (Copper Distributed Data Interface) connection. Furthermore, communications may also include links to any of a variety of wireless networks, including WAP (Wireless Application Protocol), GPRS (General Packet Radio Service), GSM (Global System for Mobile Communication), CDMA (Code Division Multiple Access) or TDMA (Time Division Multiple Access), cellular phone networks, GPS (Global Positioning System), CDPD (cellular digital packet data), RIM (Research in Motion, Limited) duplex paging network, Bluetooth radio, or an IEEE 802.11-based radio frequency network. The network 120 can further include or interface with any one or more of an RS-232 serial connection, an IEEE-1394 (Firewire) connection, a Fiber Channel connection, an IrDA (infrared) port, a SCSI (Small Computer Systems Interface) connection, a USB (Universal Serial Bus) connection or other wired or wireless, digital or analog interface or connection, mesh or Digi® networking.

The system 105 generally comprises a processor, 130, a network interface 135, and a memory 140. According to some embodiments, the memory 140 comprises logic (e.g., instructions) 145 that can be executed by the processor 130 to perform various methods. For example, the logic may include a user interface module 125 as well as a data aggregation and correlation application (hereinafter application 150) that is configured to provide the functionalities described in greater detail herein.

It will be understood that the functionalities described herein, which are attributed to the system 105 and application 150 may also be executed within the client (sensor network) 115. That is, the client (sensor network) 115 may be programmed to execute the functionalities described herein. In other instances, the system 105 and client (sensor network) 115 may cooperate to provide the functionalities described herein, such that the client (sensor network) 115 is provided with a client-side application that interacts with the system 105 such that the system 105 and client (sensor network) 115 operate in a client/server relationship. Complex computational features may be executed by the system 105, while simple operations that require fewer computational resources may be executed by the client (sensor network) 115, such as data gathering and data display.

In general, the user interface module 125 may be executed by the system 105 to provide various graphical user interfaces (GUIs) that allow users to interact with the system 105. The system 105 may generate web-based interfaces for the client.

In various embodiments of the present technology, the soil environment and ability of irrigation facilities (i.e., irrigation system) in fields are not uniform, the water movement speed and water holding capacity in the soil, and ability of water spraying from a pipeline differs depending on the location. To cover different location characteristics, the plurality of sensors (e.g., the client (sensor network) 115) described above may be installed in several different fields. The number of fields with installed sensors may need to be limited to control costs for the farmer. Thus, in various embodiments using low-cost network technology allows a farmer to put more sensors in more fields while controlling costs to generate more data for enhanced results.

In some embodiments, network 120 may be a low-cost network system including a wireless mesh network or a start network. The communications network (e.g., network 120) may be constructed using small antenna devices that transmit and receive data wirelessly. By configuring the local network wirelessly rather than wired, it is possible to introduce a wider observation network at lower cost. Various types of sensors are connected to the antenna devices, and data observed by sensors is transferred to the central computer which is mounted at the base station through the local network. After data is collected at a computer of the base station, that data is processed to apply into the soil moisture model to optimize irrigation operations, or the data is transferred from the base station to more powerful computers located remotely.

In various embodiments, the data collected from the sensor network (e.g., the client (sensor network) 115) described above may be used for a soil moisture model. In various embodiments data is collected in real-time or near real-time. Furthermore, the soil around each of the sensors of the plurality of sensors measuring the plurality of environmental elements is characterized and the soil data is analyzed and used for modeling. Specifically, the amount of water movement in the soil may be arbitrarily calculated based on the physical laws and the empirical formulas. Those rules and equations may be used to construct the soil moisture model that calculates an amount of water movement in different soil layers. The purpose of using the soil moisture model is to determine a proper amount of irrigation water or irrigation time (e.g., irrigation duration, and the like) which achieves a minimum amount of percolation under a crop rootzone. A basic formula of a soil moisture model according to various embodiments is described by Equation (1).

$$\theta(t+\Delta t) = \theta(t) + g(t) - F(t) - ET(t) \qquad \text{Equation 1}$$

$\theta(t)$: Soil moisture at time t [mm].
g(t): Infiltration at time t [mm].
F(t): Percolation at time t [mm/hour].
ET(t): Evapotranspiration at time t [mm/hour].
$\Delta t$: Difference of time step [hour]

In various embodiments, a calculation of percolation may be made using Equation (2).

$$F(t) = \frac{1}{1 + p_1 \exp(-p_2(\theta(t) - \theta_{fc}))} f_c \qquad \text{Equation (2)}$$

$f_c$: Infiltration when moisture is around field capacity [mm/hour].

$p_1$: Parameter.
$p_2$: Parameter.
$\theta_{fc}$: Moisture when soil is field capacity [mm].

In various embodiments, a calculation of evapotranspiration may be made using Equation (3).

$$ET(t) = \frac{PET}{1 + m_1 \exp(-m_2(\theta(t) - \theta_{fc}))} ET_p(t) \quad \text{Equation (1)}$$

PET: Ratio of actual ET.
$m_1$: Parameter.
$m_2$: Parameter.
$ET_p$: Parameter.

In various embodiments the soil moisture model is described by Equation (1), calculates a change of moisture per unit time. The change of moisture is composed by three factors. The first factor is infiltration (e.g., g(t)) which is an amount of water moving from the upper layer. One exemplary formula to calculate infiltration is Horton's equation. However, the soil moisture model may use other theories to calculate infiltration. The second factor is percolation (e.g., F(t)) which is an amount of water penetrating into the lower layer. The third factor is evapotranspiration (e.g., ET(t)) which is an amount of water consumed by crops or the atmosphere. These factors are described by governing equations. In each of the terms included in the right side of Equation (1), parameters depending on soil or crop characteristics exist.

In various embodiments, unknown values of parameters are determined by using an optimization algorithm to find out most probable combination of parameters. An optimization algorithm calculates outputs of a model with temporary parameters and selects the best result by fitting the outputs to minimize the residual of observation data. There are several types of optimization algorithms and an efficiency of an optimization algorithm depends on an approach of a specific optimization algorithm.

Figure 2:
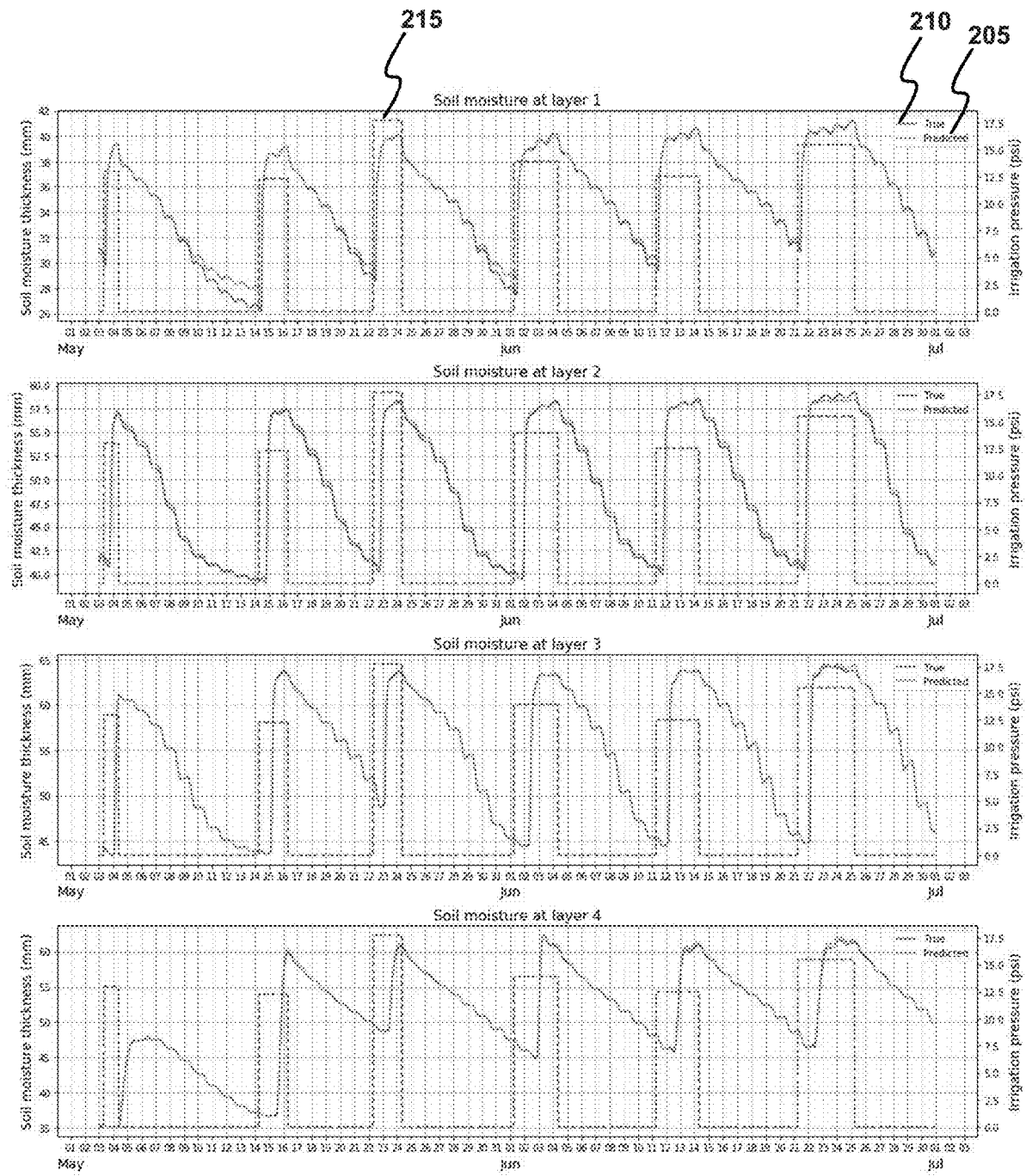
FIG. 2 shows a predicted soil moisture in a field at different layers of the soil using soil moisture modeling according to various embodiments of the present technology.

FIG. 2 shows predicted soil moisture in a field at different layers of the soil using the soil moisture model according to various embodiments of the present technology. FIG. 2 shows a predicted soil moisture 205 by the soil moisture model using Equation (1) at four soil layers. FIG. 2 includes measured soil moisture 210 (e.g., a measured soil moisture using data from a soil moisture sensor) compared with the predicted soil moisture 205 (i.e., a predicted soil moisture using the soil moisture model). In other words, the true soil moisture. FIG. 2 also shows irrigation water pressure data 215 (psi) showing the amount of water pressure in the irrigation system. For instance, six irrigation events are shown in FIG. 2 (i.e., six peaks of irrigation water pressure data 215 at all four soil layers followed by a decrease in both measured soil moisture 210 (e.g., a measured soil moisture using data from a soil moisture sensor) and the predicted soil moisture 205 (i.e., a predicted soil moisture using the soil moisture model). The measured soil moisture 210 (e.g. true soil moisture) is observed data by soil moisture sensor (i.e., measured soil moisture using data from a soil moisture sensor). The predicted soil moisture 205 is a predicted soil moisture by the soil moisture model (i.e., a predicted soil moisture using the soil moisture model.) The measured soil moisture 210 (e.g. true soil moisture) is similar to the predicted soil moisture 205 (i.e., a predicted soil moisture using the soil moisture model) demonstrating the accuracy of the soil moisture model. The data displayed in FIG. 2 were achieved after parameter calibration with a soil sensor data. The determination of coefficient was 0.997 for this data set displayed in FIG. 2.

Irrigation water or rainfall water moves into vertical direction in soil under the influence of gravity. For example, infiltration is the process by which water on the ground surface enters the soil. For example, an amount of infiltration depends on the current amount of soil moisture. For instance, if an amount of water from an upper layer of soil is larger than infiltration, not all of an amount of water can penetrate into the lower soil layer with the rest of the water remaining on the ground surface.

In various embodiments, an amount of water from rainfall or irrigation is calculated by Equation (4).

$$R(t) = P(t) + f(\text{pressure}(t)) \quad \text{Equation (4)}$$

P(t): Precipitation at time [mm/hour].
f(pressure(t)): Amount of irrigation water at time calculated by pressure [mm/hour].

For example, typically when it is raining, farmers may not turn on an irrigation system to save irrigation water, but using Equation (4), the total amount of water from rainfall and irrigation system is calculated to determine an amount of water in the top layer of soil. In fact, the amount of water from each irrigation emitter in an irrigation system may be localized and may not be uniform. For instance, a localized emitter may be caused by a problem with an irrigation pipeline such as degradation of a pipe or difference of elevation. Thus, an amount of water from an emitter in unit time is calculated by pressure data from a pipeline. For example, a pressure sensor may be installed to measure pressure (e.g., irrigation water pressure data 215 (psi) in FIG. 2) between emitters with the function of calculating an amount of water depending on the type of emitter. In some instances, flow data at the pump may be used to estimate the amount of applied water for irrigation, so other data besides pressure data may be used. According to the sensor data in field, duration of irrigation may exceed two days in exemplary embodiments.

In some instances, percolation happens when soil moisture of the current layer exceeds the near level of Field Capacity (FC). Percolation is calculated by Equation (2). The $f_c$ is a constant value infiltration when moisture is equal to FC. In one scientific definition of FC, the amount of soil moisture or water content held in the soil after excess water has drained away and the rate of downward movement has decreased. For example, FC usually takes place two to three days after rain or irrigation in pervious soils of uniform structure and texture. Thus, using this definition, percolation starts when moisture reaches to FC. However, according to soil moisture data, percolation has happened gradually, not suddenly. Therefore, in Equation (2), $f_c$ is multiplied to activation function to calculate percolation. In Equation (2), when soil moisture gets close to FC, percolation increases gradually. This non-linear relationship is described by the activation function in Equation (2). When moisture exceeds FC, ratio of percolation reaches one.

In various embodiments, if percolation happens at a deeper soil layer (i.e., a greater soil depth) than a crop rootzone, water below the crop rootzone is surplus water and is not consumed by crop growth resulting in inefficient irrigation water use. In various instances, FC may be determined after parameters of the soil moisture model are fitted. In addition, soil moisture has another threshold called Wilting Point (WP) which is lower than FC. When soil moisture reaches to the WP, plants will get severe damage and may not be able to fully recover from the WP. For example, Wilting Point (WP) may be defined as the minimum amount of water in the soil that a plant requires not to wilt. If the soil water content decreases to WP or any point below WP, a plant wilts and can no longer recover its turgidity when placed in a saturated atmosphere for twelve hours. Therefore, an optimum amount of water in soil of a crop field is a level at which the soil moisture in the crop rootzone is above WP as a minimum level and below FC, while including a sufficient amount of water to account for evapotranspiration.

In various embodiments, an actual evapotranspiration (ET) in each soil layer is calculated using Equation (3). Calculating potential ET has several methodologies such as using the FAO Penman-Montieth equation. However, the actual amount of ET consumed by crop may depend on other factors of soil moisture. For example, if soil does not contain much soil moisture, attraction from soil to water is too strong to allow crops to absorb water by their roots. Thus, an activation function similar to percolation may be applied to calculate actual ET. At the surface, surplus water by irrigation would be consumed by evaporation and not only to infiltration into the soil. However, it is difficult to account for transpiration and evaporation from ET. In this model, potential ET is multiplied by a constant ratio to simply estimate evaporation at the surface.

Figure 3:
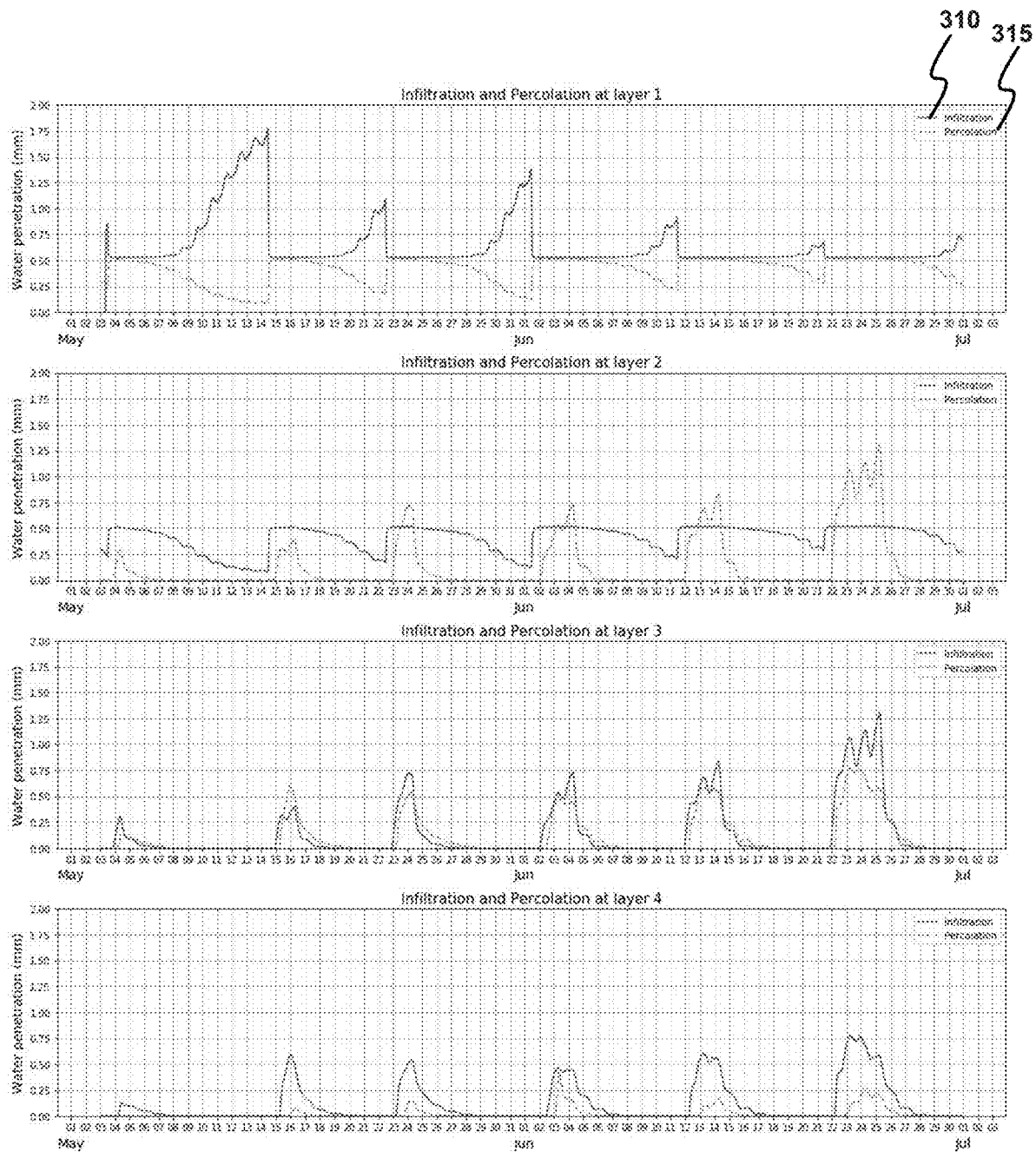
FIG. 3 shows infiltration and percolation in a field at different layers of the soil using soil moisture modeling according to various embodiments of the present technology.

FIG. 3 shows infiltration 310 and percolation 315 in a field at different layers of the soil using soil moisture modeling according to various embodiments of the present technology. For example, FIG. 3 shows infiltration 310 and percolation 315 at each of the four soil layers calculated using a soil moisture model calibrated by observation data. For instance, six irrigation events are shown in FIG. 3 that correspond to the six peaks of irrigation water pressure data 215 shown in FIG. 2 at all four soil layers followed by a decrease in measured soil moisture 210 and predicted soil moisture 205. FIG. 3 also shows that infiltration 310 and percolation 315 are decrease at lower soil levels. Furthermore, a duration length of irrigation affected the amount of the infiltration 310 and the percolation 315 at all four layers consecutively. For example, the first irrigation event (i.e., first peak) did not make percolation at the fourth layer because the length of irrigation event was shorter than a subsequent irrigation duration.

In various embodiments, to fill the crop rootzone with an optimum amount of soil moisture, it is necessary to fill the upper soil layer the Field Capacity (FC) or more and generate percolation to transport water. For example, an amount of water sprayed by the irrigation system can be obtained either by measuring with an irrigation sensor or by setting it before starting irrigation using Equation (2). Typically, the amount of irrigation water sprayed per unit time is higher than the infiltration of the topsoil layer, thus, water stagnates if the surface layer is flat. If water remains on the ground surface even after irrigation stops, the residual water calculated using Equation (4) will infiltrate into the soil layer. In exemplary embodiments, Equation (5) and Equation (8) below may be used calculate an optimal irrigation duration to provide a minimum amount of water by irrigation, including the aforementioned residual water.

In various embodiments, an optimum irrigation duration is calculated using Equation 5. An amount of water form irrigation is calculated using Equation 5.

$$w(t) = f_R \times t \quad \text{Equation (5)}$$

$f_R$: Irrigation rate [mm/hour].
t: Irrigation duration [hour].

$R_i$: Amount of water to fill from current moisture to field capacity at layer [mm].

In various embodiments, an amount of water to fill field capacity at layer is calculated using Equation 6.

$$R_l = \theta_{FC,l} - \theta_{p,l} \quad \text{Equation (6)}$$

$R_l$ Amount of water to fill from current moisture to field capacity at layer l [mm].
$\theta_{FC,l}$: Soil moisture of field capacity at layer [mm].
$\theta_{p,l}$: The present moisture at layer [mm].

In various embodiments, an amount of surplus water on the surface is calculated by Equation 7.

$$s(T) = \begin{cases} w(T) - R_1, & T < T_{FC} \\ w(T) - R_1 - f_c \times (T - T_{FC}), & T \geq T_{FC} \end{cases} \quad \text{Equation (2)}$$

$R_1$: Amount of water to fill from current moisture to field capacity at layer 1 [mm].
T: The duration of irrigation [hour].
$f_c$: Infiltration when moisture is filled by field capacity [mm/hour].
$f_e$: The duration which takes to fill moisture to field capacity.
$T_{FC}$: The duration which takes to fill moisture to field capacity.

In various embodiments, an irrigation duration is calculated by Equation 8 including an optimal irrigation duration.

$$\min_{T<0}(s(T) - \left(\sum_{l=2}^{N} R_l + ET(T)\right) \quad \text{Equation (3)}$$

N: Total number of soil layers.
ET(T): Cumulative ET for duration [mm].

In various embodiments, an optimum irrigation duration is calculated at λ=f(x).

In various embodiments the present technology allows interpolation by remote sensing. For example, using interpolation, a "parameter estimation model" may be used with parameters of a soil model as dependent variables. Independent variables may be observable by remote sensing or referenceable by a third-party dataset. For example, to determine an optimized irrigation schedule with a soil model at different locations, observational data (i.e., measured data) may be required to select valid parameters. Parameters determined by sensor data may be difficult to use at a different location because characteristics of the soil may not the same at the different location. Nonetheless, by applying a parameter estimation model at a location that a sensor is not installed, a soil model may be used without sensor data. Thus, allowing planning of an optimal irrigation schedule for fields without a sensor system installed.

Figure 4:
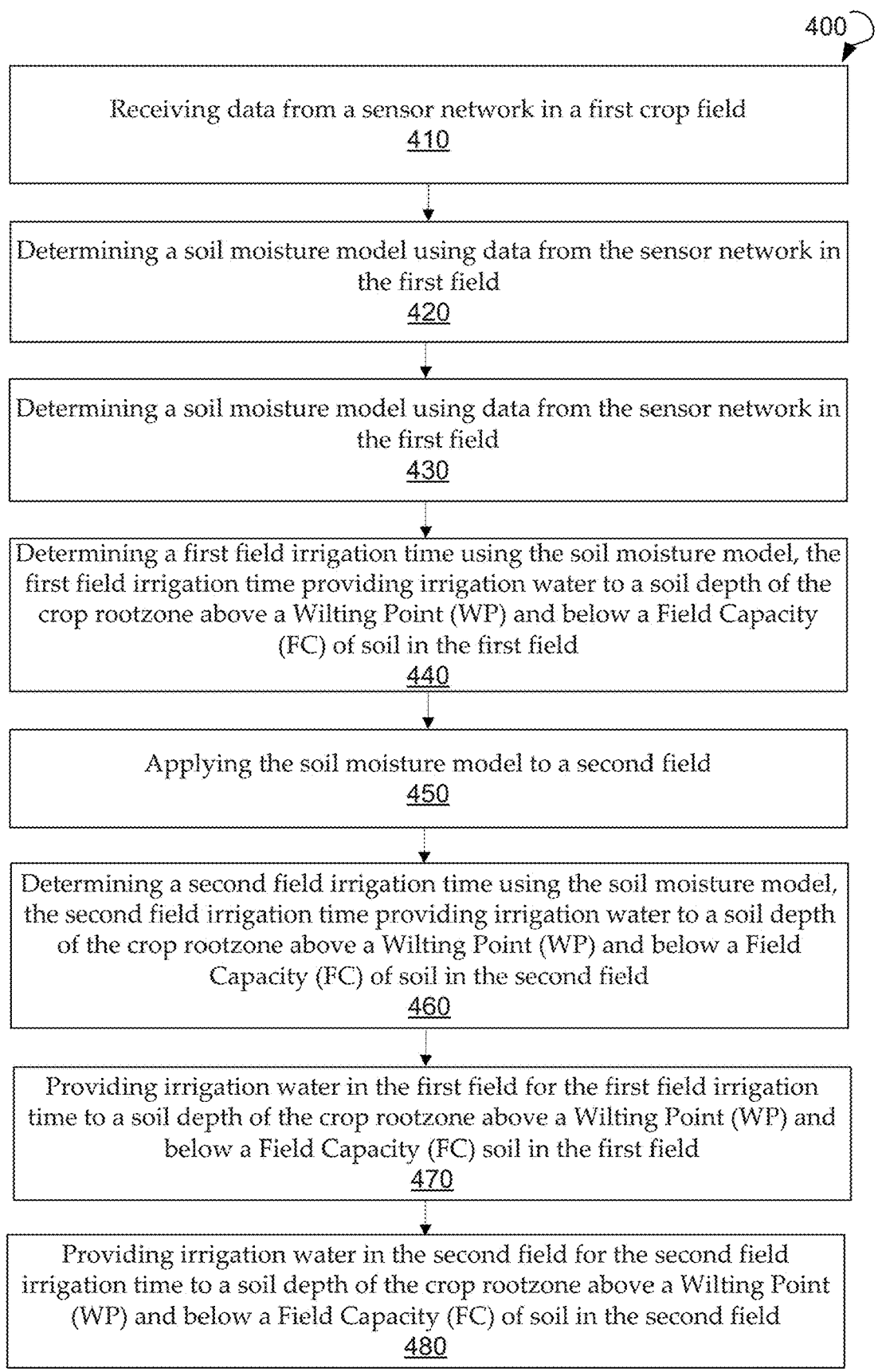
FIG. 4 show a method for providing irrigation water to a soil depth of a crop rootzone in a plurality of crop fields using a sensor network and soil moisture modeling.

FIG. 4 show a method for providing irrigation water to a soil depth of a crop rootzone in a plurality of crop fields using a sensor network and soil moisture modeling. FIG. 4 is a process flow diagram showing a method 400 for providing irrigation water to a soil depth of a crop rootzone in a plurality of crop fields using a sensor network and soil moisture modeling. The method 400 may be performed by processing logic that may comprise hardware (e.g., dedicated logic, programmable logic, and microcode), software (such as software run on a general-purpose computer system or a dedicated machine), or a combination thereof. In one or more example embodiments, the processing logic resides at the server system 105 or the client (sensor network) 115, or combinations thereof.

As shown in FIG. 4, the method 400 may commence at operation 410, receiving data from a sensor network in a first crop field. The data from the sensor network in a first crop field may include data from a soil moisture sensor in the first crop field, data from a water added sensor in the first crop field, and data from a meteorological elements sensor in the first crop field. The data for the sensor network may be monitored continuously or in set increments such as one-hour intervals.

At operation 420, the method 400 may proceed with determining a soil moisture model using data from the sensor network in the first field. The soil moisture model may be determined using Equation (1) as described above as well as using the other equations described herein.

At operation 430, the method 400 may include determining a soil moisture model using data from the sensor network in the first field. For example, data from a sensor network (i.e., client (sensor network) 115) may be used for determining a soil moisture model.

At operation 440, the method 400 may proceed with determining a first field irrigation time using the soil moisture model, the first field irrigation time providing irrigation water to a soil depth of the crop rootzone above a Wilting Point (WP) and below a Field Capacity (FC) of soil in the first field. For example, Equation (1) through Equation (8) described herein may be used to determine the first field irrigation time. In one embodiment, the first field irrigation time (i.e., an irrigation duration) is calculated by Equation 8 including an optimal irrigation duration.

At operation 450, the method 400 may proceed with applying the soil moisture model to a second field. For example, interpolation by remote sensing may be used to determine data the second field even though sensors may not be installed in the second field.

At operation 460, the method 400 may include determining a second field irrigation time using the soil moisture model, the second field irrigation time providing irrigation water to a soil depth of the crop rootzone above a Wilting Point (WP) and below a Field Capacity (FC) of soil in the second field. For example, the Equation (1) through Equation (8) described herein and interpolation by remote sensing may be used to determine the first field irrigation time. In one embodiment, the second field irrigation time (i.e., an irrigation duration) is calculated by Equation 8 including an optimal irrigation duration.

At operation 470, the method 400 may include providing irrigation water in the first field for the first field irrigation time to a soil depth of the crop rootzone above a Wilting Point (WP) and below a Field Capacity (FC) of soil in the first field. An irrigation system for providing irrigation water in the first field may include a system of pipes and emitters.

At operation 480, the method 400 may include providing irrigation water in the second field for the second field irrigation time to a soil depth of the crop rootzone above a Wilting Point (WP) and below a Field Capacity (FC) soil in the second field. An irrigation system for providing irrigation water in the second field may include a system of pipes and emitters.

Figure 5:
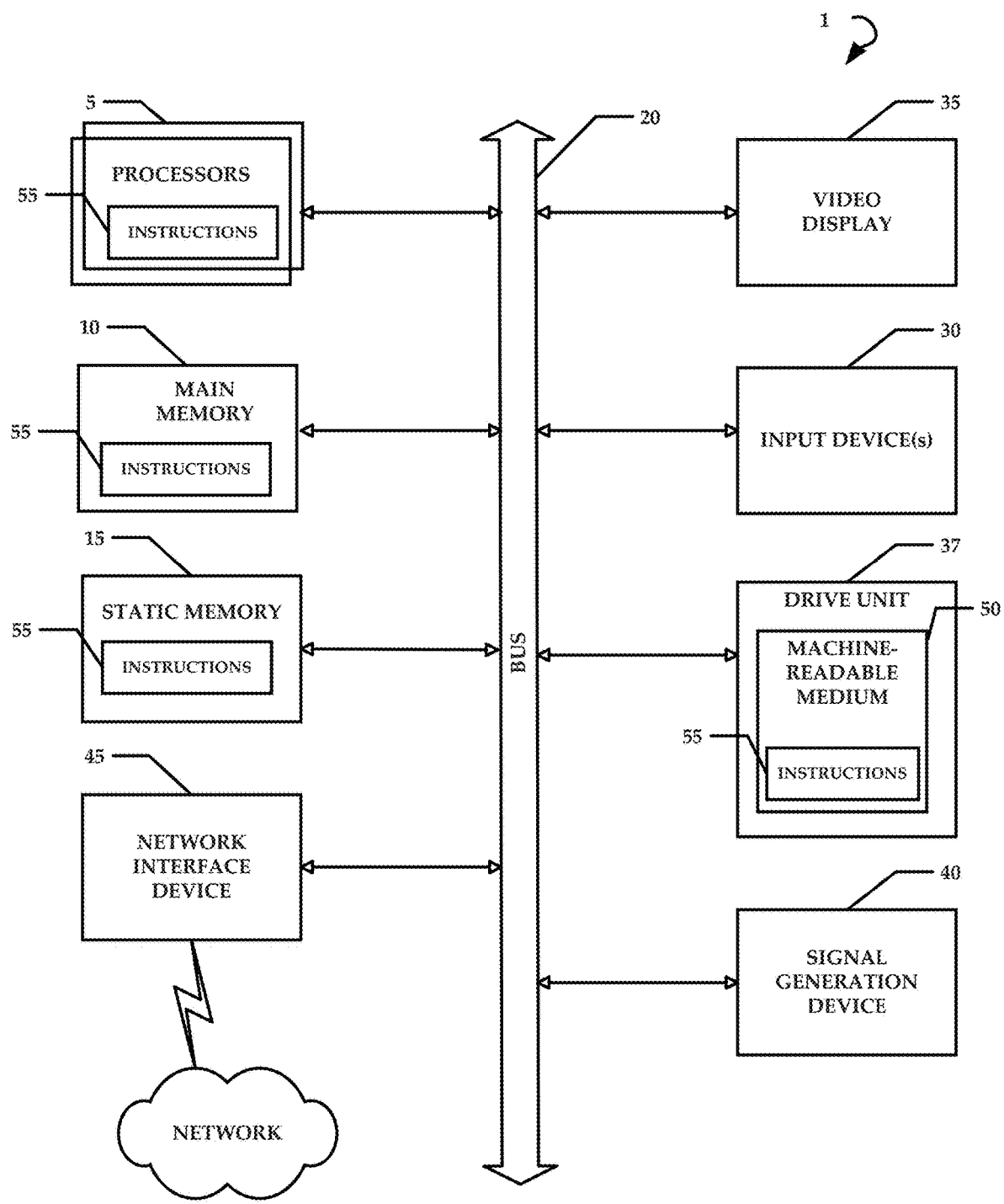
FIG. 5 illustrates an exemplary computer system that may be used to implement embodiments of the present disclosure.

FIG. 5 is a diagrammatic representation of an example machine in the form of a computer system 1, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a personal digital assistant (PDA), a cellular telephone, a portable music player (e.g., a portable hard drive audio device such as an Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1 includes a processor or multiple processor(s) 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alpha-numeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The disk drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processor(s) 5 during execution thereof by the computer system 1. The main memory 10 and the processor(s) 5 may also constitute machine-readable media.

The instructions 55 may further be transmitted or received over a network (e.g., network 120, see FIG. 1) via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

In the description, for purposes of explanation and not limitation, specific details are set forth, such as particular embodiments, procedures, techniques, etc. in order to provide a thorough understanding of the present technology. However, it will be apparent to one skilled in the art that the present technology may be practiced in other embodiments that depart from these specific details.

While specific embodiments of, and examples for, the system are described above for illustrative purposes, various equivalent modifications are possible within the scope of the system, as those skilled in the relevant art will recognize. For example, while processes or steps are presented in a given order, alternative embodiments may perform routines having steps in a different order, and some processes or steps may be deleted, moved, added, subdivided, combined, and/or modified to provide alternative or sub-combinations. Each of these processes or steps may be implemented in a variety of different ways. Also, while processes or steps are at times shown as being performed in series, these processes or steps may instead be performed in parallel or may be performed at different times.

While various embodiments have been described above, it should be understood that they have been presented by way of example only, and not limitation. The descriptions are not intended to limit the scope of the present technology to the particular forms set forth herein. To the contrary, the present descriptions are intended to cover such alternatives, modifications, and equivalents as may be included within the spirit and scope of the present technology as appreciated by one of ordinary skill in the art. Thus, the breadth and scope of a preferred embodiment should not be limited by any of the above-described exemplary embodiments.

What is claimed is:

1. A system for providing irrigation water to a soil depth of a crop rootzone in a plurality of crop fields using a sensor network and soil moisture modeling, the system comprising:
    a sensor network in a first field, comprising:
        a dendrometer in the first field;
        a soil moisture sensor in the first field;
        a water added sensor in the first field; and
        a meteorological elements sensor in the first field measuring temperature, precipitation, solar radiation, relative humidity and wind speed;
    at least one processor;
    a memory storing processor-executable instructions, wherein the at least one processor is configured to implement the following operations upon executing the processor-executable instructions:
        determining a soil moisture model using data from the sensor network in the first field, the soil moisture model computed based on:

$$\theta(t+\Delta t)=\theta(t)+g(t)-F(t)-ET(t)$$ where:

$\theta(t)$: Soil moisture at time t [mm];
        $g(t)$: Infiltration at time t [mm];
        $F(t)$: Percolation at time t [mm/hour];
        $ET(t)$: Evapotranspiration at time t [mm/hour]; and
        $\Delta t$: Difference of time step [hour];
            determining a first field irrigation time using the soil moisture model, the first field irrigation time providing the irrigation water to the soil depth of the crop rootzone above a Wilting Point (WP) and below a Field Capacity (FC) of soil in the first field;
            applying the soil moisture model to a second field; and
            determining a second field irrigation time using the soil moisture model, the second field irrigation time providing the irrigation water to the soil depth of the crop rootzone above the Wilting Point (WP) and below the Field Capacity (FC) of soil in the second field; and
    an irrigation system providing the irrigation water in the first field for the first field irrigation time to the soil depth of the crop rootzone above the Wilting Point (WP) and below the Field Capacity (FC) of soil in the first field, and providing the irrigation water in the second field for the second field irrigation time to the soil depth of the crop rootzone above the Wilting Point (WP) and below the Field Capacity (FC) of soil in the second field; wherein the first field irrigation time and the second field irrigation time provide the irrigation water above the Field Capacity (FC) for the soil depth at the crop rootzone resulting in the irrigation water percolation to the crop rootzone.

2. The system of claim 1, wherein the water added sensor measures an actual amount of water added to a field.

3. The system of claim 1, wherein the soil moisture sensor measures an amount of moisture contained in the soil at a plurality of different depths in the soil at the first field.

4. The system of claim 3, wherein the plurality of different depths in the soil at the first field include a soil depth above the crop rootzone, a soil depth at the crop rootzone, and a soil depth below the crop rootzone.

5. The system of claim 4, wherein the first field irrigation time and the second field irrigation time provide the irrigation water below the Field Capacity (FC) for the soil depth at the crop rootzone preventing the irrigation water percolation to the soil depth below the crop rootzone thereby saving the irrigation water.

6. The system of claim 4, wherein the determining the soil moisture model comprises:
    determining current soil moisture, the infiltration, the percolation, and the evapotranspiration at the soil depth above the crop rootzone in the first field using the data from the sensor network in the first field; and determining soil moisture at the soil depth above the crop rootzone in the second field using the current soil moisture, the infiltration, the percolation, and the evapotranspiration at the soil depth above the crop rootzone in the first field.

7. A method for providing irrigation water to a soil depth of a crop rootzone in a plurality of crop fields using a sensor network and soil moisture modeling, the method comprising:
receiving data from a sensor network in a first crop field, comprising:
receiving data from a dendrometer in the first crop field;
receiving data from a soil moisture sensor in the first crop field;
receiving data from a water added sensor in the first crop field; and
receiving data from a meteorological elements sensor in the first crop field measuring temperature, precipitation, solar radiation, relative humidity and wind speed;
determining a soil moisture model using the data from the sensor network in the first field, the soil moisture model computed based on:

$$\theta(t+\Delta t)=\theta(t)+g(t)-F(t)-\text{ET}(t) \quad \text{where:}$$

$\theta(t)$: Soil moisture at time t [mm];
$g(t)$: Infiltration at time t [mm];
$F(t)$: Percolation at time t [mm/hour];
$\text{ET}(t)$: Evapotranspiration at time t [mm/hour];
$\Delta t$: Difference of time step [hour];
determining a first field irrigation time using the soil moisture model, the first field irrigation time providing the irrigation water to the soil depth of the crop rootzone above a Wilting Point (WP) and below a Field Capacity (FC) of soil in the first field;
applying the soil moisture model to a second field;
determining a second field irrigation time using the soil moisture model, the second field irrigation time providing irrigation water to the soil depth of the crop rootzone above the Wilting Point (WP) and below the Field Capacity (FC) of soil in the second field;
providing the irrigation water in the first field for the first field irrigation time to the soil depth of the crop rootzone above the Wilting Point (WP) and below the Field Capacity (FC) soil in the first field; and
providing the irrigation water in the second field for the second field irrigation time to the soil depth of the crop rootzone above the Wilting Point (WP) and below the Field Capacity (FC) of soil in the second field.

8. The method of claim 7, wherein the water added sensor measures an actual amount of water added to a field.

9. The method of claim 7, wherein the soil moisture sensor measures an amount of moisture contained in the soil at a plurality of different depths in the soil at the first field.

10. The method of claim 9, wherein the plurality of different depths in the soil at the first field include a soil depth above the crop rootzone, a soil depth at the crop rootzone, and a soil depth below the crop rootzone.

11. The method of claim 10, wherein the first field irrigation time and the second field irrigation time provide the irrigation water above the Field Capacity (FC) for the soil depth at the crop rootzone resulting in the irrigation water percolation to the crop rootzone.

12. The method of claim 10, wherein the first field irrigation time and the second field irrigation time provide the irrigation water below the Field Capacity (FC) for the soil depth at the crop rootzone preventing the irrigation water percolation to the soil depth below the crop rootzone thereby saving the irrigation water.

13. The method of claim 10, wherein the determining the soil moisture model comprises:
determining current soil moisture, the infiltration, the percolation, and the evapotranspiration at the soil depth above the crop rootzone in the first field using the data from the sensor network in the first field; and
determining soil moisture at the soil depth above the crop rootzone in the second field using the current soil moisture, the infiltration, the percolation, and the evapotranspiration at the soil depth above the crop rootzone in the first field.

14. A non-transitory computer readable medium having embodied thereon instructions being executable by at least one processor to perform a method for providing irrigation water to a soil depth of a crop rootzone in a plurality of crop fields using a sensor network and soil moisture modeling, the method comprising:
receiving data from a sensor network in a first crop field, comprising:
receiving data from a dendrometer in the first crop field;
receiving data from a soil moisture sensor in the first crop field;
receiving data from a water added sensor in the first crop field; and
receiving data from a meteorological elements sensor in the first crop field measuring temperature, precipitation, solar radiation, relative humidity and wind speed;
determining a soil moisture model using the data from the sensor network in the first field, the soil moisture model computed based on:

$$\theta(t+\Delta t)=\theta(t)+g(t)-F(t)-\text{ET}(t) \quad \text{where:}$$

$\theta(t)$: Soil moisture at time t [mm];
$g(t)$: Infiltration at time t [mm];
$F(t)$: Percolation at time t [mm/hour];
$\text{ET}(t)$: Evapotranspiration at time t [mm/hour];
$\Delta t$: Difference of time step [hour];
determining a first field irrigation time using the soil moisture model, the first field irrigation time providing irrigation water to the soil depth of the crop rootzone above a Wilting Point (WP) and below a Field Capacity (FC) of soil in the first field;
applying the soil moisture model to a second field;
determining a second field irrigation time using the soil moisture model, the second field irrigation time providing the irrigation water to the soil depth of the crop rootzone above the Wilting Point (WP) and below the Field Capacity (FC) of soil in the second field;
providing the irrigation water in the first field for the first field irrigation time to a soil depth of the crop rootzone above the Wilting Point (WP) and below the Field Capacity (FC) of soil in the first field; and
providing the irrigation water in the second field for the second field irrigation time to a soil depth of the crop rootzone above the Wilting Point (WP) and below the Field Capacity (FC) of soil in the second field.

15. The non-transitory computer readable medium of claim 14, wherein the soil moisture sensor measures an amount of moisture contained in the soil at a plurality of different depths in the soil at the first field.

16. The non-transitory computer readable medium of claim 15, wherein the plurality of different depths in the soil at the first field include a soil depth above the crop rootzone, a soil depth at the crop rootzone, and a soil depth below the crop rootzone.

17. The non-transitory computer readable medium of claim 16,
   wherein the first field irrigation time and the second field irrigation time provide the irrigation water above the Field Capacity (FC) for the soil depth at the crop rootzone resulting in the irrigation water percolation to the crop rootzone; and
   wherein the first field irrigation time and the second field irrigation time provide the irrigation water below the Field Capacity (FC) for the soil depth at the crop rootzone preventing the irrigation water percolation to the soil depth below the crop rootzone thereby saving the irrigation water.

* * * * *